United States Patent [19]

Karrenbauer et al.

[11] Patent Number: 4,602,096
[45] Date of Patent: Jul. 22, 1986

[54] PROCESS FOR THE RACEMIZATION OF N-ACETYL-D,L-α-AMINOCARBOXYLIC ACIDS

[75] Inventors: Michael Karrenbauer, Moos-Bankholzen; Axel Kleemann, Mühlheim, both of Fed. Rep. of Germany

[73] Assignee: Degussa Aktiengesellschaft, Frankfurt, Fed. Rep. of Germany

[21] Appl. No.: 764,993

[22] Filed: Aug. 12, 1985

[30] Foreign Application Priority Data

Sep. 25, 1984 [DE] Fed. Rep. of Germany ....... 3435095

[51] Int. Cl.$^4$ ..................... C07D 209/20; C07B 55/00
[52] U.S. Cl. ..................... 548/498; 562/401; 562/450; 562/559; 562/567; 562/570; 562/573
[58] Field of Search .................... 562/401; 548/498

[56] References Cited

U.S. PATENT DOCUMENTS

| | | | |
|---|---|---|---|
| 2,071,327 | 2/1937 | Bley | 562/401 |
| 3,213,106 | 10/1965 | Sasaji et al. | 562/401 X |
| 3,458,568 | 7/1969 | Ogasawara et al. | 562/401 |
| 3,737,454 | 6/1973 | Chibata et al. | 562/401 |

*Primary Examiner*—Natalie Trousof
*Assistant Examiner*—Vera C. Clarke
*Attorney, Agent, or Firm*—Cushman, Darby & Cushman

[57] ABSTRACT

N-acetyl-D(L)-α-aminocarboxylic acids are thermally racemized by melting, adding a small amount of acetic anhydride to the melt and heating to a temperature between the melting temperature and about 210° C. and subsequently quenching the melt with an aqueous alkali metal hydroxide or ammonia solution. The residence time needed for complete racemization depends on the heating temperature of the melt in the manner that the higher the heating temperature the shorter the residence time.

9 Claims, No Drawings

4,602,096

PROCESS FOR THE RACEMIZATION OF N-ACETYL-D,L-α-AMINOCARBOXYLIC ACIDS

BACKGROUND OF THE INVENTION

The invention is directed to a process for the racemization of N-acetyl-D(L)-α-aminocarboxylic acids by heating their melts at high temperatures.

Such N-acetyl-D(L)-α-aminocarboxylic acids are obtained in the form of their salts in the enzymatic hydrolysis of the salts of N-acetyl-D,L-α-aminocarboxylic acids by means of an L-aminoacid acylase. They consist predominantly of N-acetyl-D-α-aminocarboxylics and in addition can also contain small amounts of the corresponding N-acetyl-L-α-aminocarboxylic acids. They are generally racemized after separation of the L-α-aminocarboxylic acid formed in the hydrolysis and employed again for the enzymatic cleavage.

It is already known to racemize N-acetyl-D(L)-α-aminocarboxylic acids by heating their melts to high temperatures. However, to obtain a complete racemization, relatively large residence times are required which lead to a strong discoloration and to the formation of considerable amounts of decomposition products.

SUMMARY OF THE INVENTION

The process of the invention comprises adding to the melt 0.1 to 2 weight percent, based on the N-acetyl-D(L)-α-aminocarboxylic acid, of acetic anhydride and then heating for a residence (dwell) time $\tau$ (in minutes) to a temperature between 115° and 210° C., whereby the melting temperature of the N-acetyl-D(L)-α-aminocarboxylic acid is the lower limit of the heating temperature T (in °C.) and the heating temperature and residence time are correlated by the relationship:

$$T = \ln(e^{-50\tau + 215} + e^{-5/3\tau + 155})$$

and the melt is quenched after the end of the residence time with an aqueous alkali metal hydroxide or ammonia solution. Illustrative alkali metal hydroxides are sodium hydroxide and potassium hydroxide.

Illustrative N-acetyl compounds are N-acetyl-D(L)-methionine, N-acetyl-D(L)-alanine, N-acetyl-D(L)-phenylalanine, N-acetyl-D(L)-valine, N-acetyl-D(L)-leucine, N-acetyl-D(L)-isoleucine, N-acetyl-D(L)-serine, N-acetyl-D(L)-threonine, N-acetyl-D(L)-cysteine, N-acetyl-D(L)-glutamic acid and N-acetyl-D(L)-tyrtophane.

Preferably, the acetic anhydride is added to the melt in an amount between 0.5 and 1 weight percent. Advantageously, there is chosen as heating temperature for the melt treated with acetic anhydride a temperature which is 5° to 10° C. above the melting temperature of the particular N-acetyl-D(L)-α-aminocarboxylic acid employed. The melting of the N-acetyl-D(L)-α-aminocarboxylic acid and the heating of the melt are preferably carried out under nitrogen. However, the melting and the heating of the melt can also be carried out without a protective gas or in a vacuum.

Unexpectedly, the process of the invention requires only relatively short residence times for a practically complete racemization, which times are considerably less than those which must be used in heating the melt in the absence of acetic anhydride. As a result, discoloration and the formation of decomposition products is substantially avoided.

The N-acetyl-D(L)-α-aminocarboxylic acids employed in the process of the invention are suitably obtained by sending the solution formed by enzymatic hydrolysis over a strong acid ion exchanger which adsorbs the cations present and the L-α-aminocarboxylic acid. The solution leaving the ion exchanger then consists practically of only water, acetic acid, and the N-acetyl-D(L)-α-aminocarboxylic acid. It is evaporated to dryness while maintaining the shortest possible residence times, for example, by a combination of a falling film evaporator and a thin film evaporator having a solid material discharge, and the N-acetyl-D(L)-α-aminocarboxylic acid is subjected to the treatment of the invention in this form.

Also, the residence time required for melting the N-acetyl-D(L)-α-aminocarboxylic acid suitably should be maintained as short as possible. If the melting is undertaken in a heated extruder, then generally a residence time of less than one minute suffices for the complete melting. In this case, the extruder can convey the melt into a heated reaction tube, where at the beginning of the residence zone a correspondingly designed pump continuously doses in the required amount of acetic anhydride via a mixing system.

After the end of the residence time needed for the racemization, calculated from the addition of the acetic anhydride, the melt is quenched with an aqueous alkali metal hydroxide or ammonia solution. Thereby, it is suitable to establish the same concentrate of substrate which is required for the subsequent repeated enzymatic cleavage.

The invention is explained in more detail in the following examples. Unless otherwise indicated, all percents are by weight.

The process can comprise, consist essentially of, or consist of the recited steps with the stated materials.

DETAILED DESCRIPTION

The N-acetyl-D(L)-α-amino-carboxylic acids employed and the racemized samples in each case were investigated as to their specific rotation $[\alpha]_D^{20}$ in degrees·cm³/dm·g.

EXAMPLE 1

10 grams (0.053 mole) of N-acetyl-D(L)-methionine (melting temperature ~108° C.) were melted at 118° C. under nitrogen in a forced conveyer auxiliary heated extruder within a residence time of one minute.

The melt was treated with 0.1 gram of acetic anhydride and subsequently stirred for 21 minutes more at 120° C. under nitrogen, then quenched with about 80 ml of a 1 percent aqueous ammonia solution, whereby the temperature dropped to about 40° C. The solution was adjusted to pH 7 by addition of further aqueous ammonia and by dosing in of water adjusted to the substrate concentration (0.6 molar) employed in the enzymatic reaction.

The content of N-acetyl-D,L-methionine determined by high pressure liquid chromatography was 99.1% of theory.

$[\alpha]_D^{20}$ before the racemization: +17.85° (c=4 in water).

$[\alpha]_D^{20}$ after the racemization: ±0° (c=4 in water).

EXAMPLE 2

Example 1 was repeated with the difference that the melt obtained at 118° C. subsequently was heated in a vacuum for 18 minutes at 125° C.

The content of N-acetyl-D,L-methionine determined by high pressure liquid chromatography was 97.3% of theory.

$[\alpha]_D^{20}$ before the racemization: +17.85° (c=4 in water).

$[\alpha]_D^{20}$ after the racemization: ±0° (c=4 in water).

EXAMPLE 3

Example 1 was repeated with the difference that the N-acetyl-D(L)-methionine was melted in an auxiliary heated extruder in continuous manner at 160° C. without a protective gas within a residence time of 30 seconds. The melt was treated with 0.05 gram of acetic anhydride and heated for another 1.5 minutes at 160° C. in a reaction tube connected at the outlet side.

The content of N-acetyl-D,L-methionine determined by high pressure liquid chromatography was 98.5% of theory.

$[\alpha]_D^{20}$ before the racemization: +17.85° (c=4 in water).

$[\alpha]_D^{20}$ after the racemization: ±0° (c=4 in water).

EXAMPLE 4

Example 1 was repeated with the difference that the N-acetyl-D(L)-methionine was melted at 200° C. in a forced conveyer auxiliary heated extruder in continuous manner within a residence time of 45 seconds. The melt was treated with 0.05 gram of acetic anhydride and heated at 200° C. for a further 18 seconds in a reaction tube connected at the outlet side.

The content of N-acetyl-D,L-methionine determined by high pressure liquid chromatography was 96.2% of theory.

$[\alpha]_D^{20}$ before the racemization: +17.85° (c=4 in water).

$[\alpha]_D^{20}$ after the racemization: ±0° (c=4 in water).

EXAMPLE 5

Example 1 was repeated with the difference that the N-acetyl-D(L)-methionine was melted at 115° C. The melt was treated with 0,1 gram of acetic anhydride and heated for annother 24 minutes at 115° C.

The content of N-acetyl-D,L-methionine determined by high pressure liquid chromatography was 99% theory.

$[\alpha]_D^{20}$ before the racemization: +17.85 (c=4 in water).

$[\alpha]_D^{20}$ after the racemization: ±0° (c=4 in water).

COMPARISON EXPERIMENT 1

Example 1 was repeated with the difference that the melt obtained at 118° C. was treated with 0.5 gram of acetic anhydride and subsequently was heated for another 18 minutes at 125° C.

The content of N-acetyl-D,L-methionine determined by high pressure liquid chromatography was 93% of theory.

$[\alpha]_D^{20}$ before the racemization: +17.85° (c=4 in water).

$[\alpha]_D^{20}$ after the racemization: ±0° (c=4 in water).

EXAMPLE 6

10 grams (0.076 mole) of N-acetyl-D(L)alanine (melting temperature ~130° C.) was melted at 135° C. in a forced conveyer auxiliary heated extruder within a residence time of one minute.

The melt was treated with 0.1 gram of acetic anhydride and subsequently stirred under nitrogen for another 12 minutes at 135° C. and then quenched with 50 ml of 4 percent aqueous sodium hydroxide. The further working up was carried out in a manner analogous to Example 1.

The content of N-acetyl-D,L-alanine determined by high pressure liquid chromatography was 99.2% of theory.

$[\alpha]_D^{20}$ before the racemization: +65.4° (c=2 in water).

$[\alpha]_D^{20}$ after the racemization: +0.1° (c=2 in water).

EXAMPLE 7

Example 6 was repeated with the difference that the N-acetyl-D(L)-alanine was melted in an auxiliary heated extruder in continuous manner at 170° C. within a residence time of 50 seconds. The melt was treated with 0.05 gram of acetic anhydride and heated for about one minute longer at 170° C. in a reaction tube connected at the outlet side.

The content of N-acetyl-D,L-alanine determined by high pressure liquid chromatography was 98.7% of theory.

$[\alpha]_D^{20}$ before the racemization: +65.4° (c=2 in water).

$[\alpha]_D^{20}$ after the racemization: +0.4° (c=2 in water).

COMPARISON EXPERIMENT 2

Example 6 was repeated with the difference that the melt obtained at 135° C. was treated with 0.5 gram of acetic anhydride and subsequently was stirred for another 12 minutes at 135° C.

The content of N-acetyl-D-L-alanine determined by high pressure liquid chromatography was 92.7% of theory.

$[\alpha]_D^{20}$ before the racemization: +65.4° (c=2 in water).

$[\alpha]_D^{20}$ after the racemization: ±0° (c=2 in water).

EXAMPLE 8

20 grams (0.097 mole) of N-acetyl-D(L)-phenylalanine (melting temperature ~167° C.) was melted at 175° C. under nitrogen in an auxiliary heated extruder within a residence time of 45 seconds.

The melt was treated with 0.1 gram of acetic anhydride and subsequently held at 170° C. for an additional 55 seconds in a reaction tube connected at the outlet end, and then quenched with 90 ml of 4 percent aqueous sodium hydroxide. The solution was adjusted to pH 7 by the addition of more aqueous sodium hydroxide and by the feeding in of water adjusted to the substrate concentration (0.4 molar) employed in the enzymatic cleavage.

The content of N-acetyl-D,L-phenylalanine determined by high pressure liquid chromatography was 99% of theory.

$[\alpha]_D^{20}$ before the racemization: −46.85° (c=2 in ethanol).

$[\alpha]_D^{20}$ after the racemization: ±0° (c=2 in ethanol).

EXAMPLE 9

Example 8 was repeated with the difference that the melt obtained at 175° C. was treated with 0.2 gram of acetic anhydride and subsequently was heated at 175° C. for another 50 seconds.

The content of N-acetyl-D,L-phenylalanine determined by high pressure liquid chromatography was 98.5% of theory.

$[\alpha]_D^{20}$ before the racemization: $-46.85°$ (c=2 in ethanol).

$[\alpha]_D^{20}$ after the racemization: $\pm 0°$ (c=2 in ethanol).

EXAMPLE 10

Example 8 was repeated with the difference that the melt obtained at 175° C. was treated with 0.4 gram of acetic anhydride and subsequently was held at 170° C. for an additional 50 seconds.

The content of N-acetyl-D,L-phenylalanine determined by high pressure liquid chromatography was 97.5% of theory.

$[\alpha]_D^{20}$ before the racemization: $-46.85°$ (c=2 in ethanol).

$[\alpha]_D^{20}$ after the racemization: $\pm 0°$ (c=2 in ethanol).

COMPARISON EXPERIMENT 3

Example 10 was repeated with the difference that the melt was treated with 1.0 gram of acetic anhydride.

The content of N-acetyl-D,L-phenylalanine determined by high pressure liquid chromatography was 92.2% of theory.

$[\alpha]_D^{20}$ before the racemization: $-46.85°$ (c=2 in ethanol).

$[\alpha]_D^{20}$ after the racemization: $\pm 0°$ (c=2 in ethanol).

EXAMPLE 11

10 grams (0.041 mole) of N-acetyl-D(L)-tryptophane (melting temperature ~193° C.) were melted at 205° C. under nitrogen in an auxiliary heated extruder within a residence time of 45 seconds.

The melt was treated with 0.05 gram of acetic anhydride and subsequently held at 205° C. for an additional 12 seconds in a reaction tube connected at the outlet end and subsequently quenched with 150 ml of 1 percent aqueous sodium hydroxide and adjusted to the substrate concentration (0.2 molar) employed in the enzymatic cleavage.

The NMR spectrum was identical with that of the starting material which indicates a content of N-acetyl-D,L-tryptophane of at least 95% of theory.

$[\alpha]_D^{20}$ before the racemization: $-23.0°$ (c=5 in methanol).

$[\alpha]_D^{20}$ after the racemization: $-0.02°$ (c=5 in methanol).

EXAMPLE 12

10 grams (0.063 mole) of N-acetyl-D(L)-valine (melting temperature ~162° C.) were melted at 170° C. under nitrogen in an auxiliary heated extruder within a residence time of 40 seconds.

The melt was treated with 0.05 gram of acetic anhydride and subsequently held for an additional 55 seconds at 170° C. in a reaction tube connected at the outlet end and subsequently quenched with 50 ml of a 4 percent aqueous sodium hydroxide. The further processing was carried out in a manner analogous to Example 1.

The content of N-acetyl-D,L-valine determined by high pressure liquid chromatography was 99.1% of theory.

$[\alpha]_D^{20}$ before the racemization: $+17.7°$ (c=4 in water).

$[\alpha]_D^{20}$ after the racemization: $+0.6°$ (c=4 in water).

The entire disclosure of German priority application P3435095.0 is hereby incorporated by reference.

What is claimed is:

1. A process for the racemization of an N-acetyl-D(L)-α-aminocarboxylic acid comprising heating a melt of the aminocarboxylic acid at an elevated temperature with 0.1 to 2 weight percent of acetic anhydride based on the N-acetyl-D(L)-α-aminocarboxylic acid and then heating it for a residence time, in minutes, to a temperature between 115° and 210° C. wherein the melting temperature of the N-acetyl-D(L)-α-aminocarboxylic acid is the lower limit of the heating temperature T, in °C., and the heating temperature and residence time are correlated by the relationship:

$$T = \ln(e^{-50\tau + 215} + e^{-5/3\tau + 155})$$

and quenching the melt after the end of the residence time with an aqueous alkali metal hydroxide or ammonia solution.

2. A process according to claim 1 wherein there is added to the melt 0.5 to 1 weight percent of acetic anhydride.

3. A process according to claim 2 wherein the heating of the melt is carried out at a temperature which is 5° to 10° C. above the melting temperature of the N-acetyl-D(L)-α-aminocarboxylic acid.

4. A process according to claim 1 wherein the heating of the melt is carried out at a temperature which is 5° to 10° C. above the melting temperature of the N-acetyl-D(L)-α-aminocarboxylic acid.

5. A process according to claim 4 comprising carrying out the melting of the N-acetyl-D(L)-α-aminocarboxylic acid and the heating of the melt under nitrogen.

6. A process according to claim 3 comprising carrying out the melting of the N-acetyl-D(L)-α-aminocarboxylic acid and the heating of the melt under nitrogen.

7. A process according to claim 2 comprising carrying out the melting of the N-acetyl-D(L)-α-aminocarboxylic acid and the heating of the melt under nitrogen.

8. A process according to claim 1 comprising carrying out the melting of the N-acetyl-D(L)-α-aminocarboxylic acid and the heating of the melt under nitrogen.

9. A process according to claim 1 wherein the N-acetyl-D(L)-α-aminocarboxylic acid is N-acetyl-D(L)-methionine, N-acetyl-D(L)-alanine, N-acetyl-D(L)-phenylalanine, N-acetyl-D(L)-tryptophane or N-acetyl-D(L)-valine.

* * * * *